United States Patent [19]
Cramp et al.

[11] Patent Number: 5,856,274
[45] Date of Patent: *Jan. 5, 1999

[54] 4-BENZOYL ISOXAZOLES AND THEIR USE AS HERBICIDES

[75] Inventors: Susan Mary Cramp, Ongar, United Kingdom; Claude Lambert, Lyon, France; Derek Ian Wallis; Thomas Yarwood, both of Ongar, United Kingdom

[73] Assignee: Rhone-Poulenc Agriculture Limited, Ongar, England

[ * ] Notice: This patent issued on a continued prosecution application filed under 37 CFR 1.53(d), and is subject to the twenty year patent term provisions of 35 U.S.C. 154(a)(2).

[21] Appl. No.: 495,455

[22] Filed: Sep. 14, 1995

[30] Foreign Application Priority Data

Feb. 3, 1993 [GB] United Kingdom ............... 9302071

[51] Int. Cl.⁶ .................... A01N 43/74; C07D 261/08
[52] U.S. Cl. ............................ 504/271; 548/248
[58] Field of Search .............. 548/248; 504/271

[56] References Cited

FOREIGN PATENT DOCUMENTS 0418175  3/1991  European Pat. Off. .
0487357  5/1992  European Pat. Off. .

OTHER PUBLICATIONS

Cram and Hammond, "Organic Chemistry", McGraw–Hill Book Co., NY (1964) 2nd Ed, pp. 565–567.

*Primary Examiner*—Patricia L. Morris
*Attorney, Agent, or Firm*—Burns, Doane, Swecker & Mathis, L.L.P.

[57] ABSTRACT

The invention relates to 4-benzoylisoxazoles having the formula:

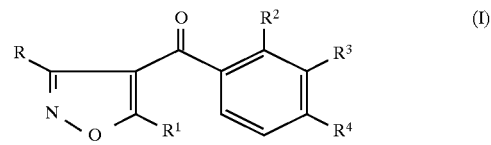

wherein:

R is hydrogen or —$CO_2R^5$;

$R^1$ is alkyl, cyclopropyl or 1-methylcyclopropyl;

$R^2$ is chlorine, bromine, optionally substituted alkyl, alkoxy, haloalkoxy, —$S(O)_pR^{61}$, nitro or cyano;

$R^3$ is —$S(O)_nR^6$;

$R^4$ is hydrogen, fluorine, chlorine, bromine, optionally substituted alkyl, alkoxy, $S(O)_qR^{61}$, nitro, cyano or —$CO_2R^{52}$;

$R^5$ and $R^{61}$, which are the same or different, are each alkyl or haloalkyl;

$R^{52}$ is alkyl;

$R^6$ is alkyl, alkenyl or alkynyl optionally substituted by one or more halogen; and n, p and q, which are the same or different, are each zero, one or two;

and their use as herbicides.

11 Claims, No Drawings

4-BENZOYL ISOXAZOLES AND THEIR USE AS HERBICIDES

This application is a 371 of PCT/EP94/00266, filed Jan. 31, 1994.

FIELD OF THE INVENTION

This invention relates to novel 4-benzoylisoxazole derivatives, compositions containing them, processes for their preparation, intermediates in their preparation and their use as herbicides.

BACKGROUND ART

Herbicidal 4-benzoylisoxazoles are described in European Patent Publication Numbers 0418175 and 0487357. Each publication in part generically discloses the compounds of the present invention. However neither publication discloses species falling within the scope of this invention, which therefore represents (in part) a novel selection from within these publications.

DESCRIPTION OF THE INVENTION

The present invention provides 4-benzoylisoxazole derivatives of formula (I):

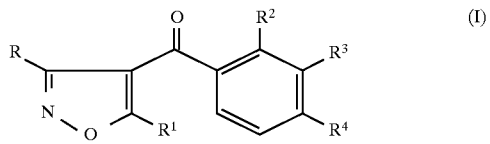

wherein R represents the hydrogen atom or a group —$CO_2R^5$;

$R^1$ represents a straight- or branched-chain alkyl group containing up to three carbon atoms; cyclopropyl or 1-methylcyclopropyl;

$R^2$ represents:
a chlorine or bromine atom;
a straight- or branched-chain alkyl group containing up to four carbon atoms which is optionally substituted by one or more halogen atoms or one or more groups —$OR^{51}$;
a straight- or branched-chain alkoxy group containing up to four carbon atoms which is optionally substituted by one or more halogen atoms; or
a group selected from —$S(O)_pR^{61}$, nitro and cyano;

$R^3$ represents a group —$S(O)_nR^6$;

$R^4$ represents:
a hydrogen, fluorine, chlorine or bromine atom;
a straight- or branched-chain alkyl group containing up to four carbon atoms which is optionally substituted by one or more halogen atoms or one or more groups —$OR^{51}$:
a straight- or branched-chain alkoxy group containing up to four carbon atoms which is optionally substituted by one or more halogen atoms; or
a group selected from —$S(O)_qR^{61}$, nitro, cyano and —$CO_2R^{52}$;

$R^5$ and $R^{61}$, which may be the same or different, each represents a straight- or branched-chain alkyl group containing up to six carbon atoms which is optionally substituted by one or more halogen atoms;

$R^{51}$ represents a straight- or branched-chain alkyl group containing up to four carbon atoms which is optionally substituted by one or more halogen atoms;

$R^{52}$ represents a straight- or branched-chain alkyl group containing up to four carbon atoms;

$R^6$ represents a straight- or branched-chain alkyl, alkenyl or alkynyl group containing up to six carbon atoms which is optionally substituted by one or more halogen atoms;

n, p and q, which may be the same of different, each represents zero, one or two;

provided that when $R^2$ represents —$S(O)_pR^{61}$ one of the groups n and p represents zero;

which possess valuable herbicidal properties.

Furthermore in certain cases the groups R, $R^1$, $R^2$, $R^3$, $R^4$, $R^5$, $R^{51}$, $R^{52}$, $R^6$ and $R^{61}$ may give rise to optical isomers. All such forms are embraced by the present invention.

The compounds of the invention, in some aspects of their activity, for example in their control of important weeds including foxtail (*Setaria viridis* and *Setaria faberii*), barnyard grass (*Echinochloa crus-galli*), wild oats (*Avena fatua*) and blackgrass (*Alopercurus myosuroides*), and in their selectivity in certain important crops, show advantages over known compounds.

DETAILED DESCRIPTION OF THE INVENTION

A preferred class of compounds of formula (I) are those wherein:

$R^2$ represents:
a chlorine or bromine atom;
a straight- or branched-chain alkyl group containing up to four carbon atoms which is optionally substituted by one or more halogen atoms:
a straight- or branched-chain alkoxy group containing up to four carbon atoms which is optionally substituted by one or more halogen atoms; or
a group —$S(O)_pR^{61}$;

$R^4$ represents:
a hydrogen, fluorine, chlorine or bromine atom;
a straight- or branched-chain alkyl group containing up to four carbon atoms which is optionally substituted by one or more halogen atoms;
a straight- or branched-chain alkoxy group containing up to four carbon atoms which is optionally substituted by one or more halogen atoms; or
a group —$S(O)_qR^{61}$;

$R^{61}$ represents a straight- or branched-chain alkyl group containing up to four carbon atoms;

$R^5$ represents a straight- or branched-chain alkyl group containing up to six carbon atoms;

$R^{52}$ represents a methyl or ethyl group;

$R^6$ represents a straight- or branched-chain alkyl, alkenyl or alkynyl group containing up to four carbon atoms; and when $R^2$ represents —$S(O)_pR^{61}$, $R^4$ represents a group other than —$S(O)_qR^{61}$.

A further preferred class of compounds of formula (I) are those wherein $R^1$ represents a cyclopropyl group;

$R^2$ represents:
a chlorine or bromine atom;
an alkyl group containing one or two carbon atoms which is optionally substituted by one or more halogen atoms;
an alkoxy group containing one or two carbon atoms which is optionally substituted by one or more halogen atoms; or
a group —$S(O)_pR^{61}$;

$R^4$ represents:
a fluorine, chlorine or bromine atom;

an alkyl group containing one or two carbon atoms which is optionally substituted by one or more halogen atoms;
an alkoxy group containing one or two carbon atoms which is substituted by one or more halogen atoms; or
a group —S(O)$_q$R$^{61}$;
R$^{61}$ represents a methyl or ethyl group;
R$^5$ represents a straight- or branched-chain alkyl group containing up to six carbon atoms;
R$^{51}$ represents a methyl or ethyl group;
R$^{52}$ represents a methyl or ethyl group;
R$^6$ represents a methyl or ethyl group; and
when R$^2$ represents —S(O)$_p$R$^{61}$, R$^4$ represents a group other than —S(O)$_q$R$^{61}$.

Particularly important compounds of formula (I) include the following:
1. 4-[2,3-bis(methylsulphenyl)-4-chlorobenzoyl]-5-cyclopropylisoxazole;
2. 4-[4-chloro-3-(methylsulphenyl)-2-(methylsulphonyl)benzoyl]-5-cyclopropylisoxazole;
3. 5-cyclopropyl-4-[2,4-dichloro-3-(methylsulphonyl)benzoyl]isoxazole;
4. 5-cyclopropyl-4-[3,4-bis(methylsulphenyl)-2-trifluoromethylbenzoyl]isoxazole
5. 5-cyclopropyl-4-[3-(methylsulphenyl)4-(methylsulphonyl)-2-trifluoromethylbenzoyl]isoxazole;
6. 5-cyclopropyl-4-[3,4-bis(methylsulphonyl)-2-trifluoromethylbenzoyl]isoxazole;
7. 4-[4-chloro-3-(methylsulphenyl)-2-trifluoromethylbenzoyl]-5-cyclopropylisoxazole;
8. 4-[4-chloro-2-(methylsulphonyl)-3-(prop-2-enylsulphenyl)benzoyl]-5-cyclopropylisoxazole;
9. 4-[4-bromo-3-(methylsulphenyl)-2-(methylsulphonyl)benzoyl]-5-cyclopropylisoxazole;
10. 4-[2,3-bis(methylsulphenyl)-4-bromobenzoyl]-5-cyclopropylisoxazole;
11. 4-[4-chloro-3-(methylsulphonyl)-2-trifluoromethylbenzoyl]-5-cyclopropylisoxazole;
12. 4-[4-chloro-3-(methylsulphenyl)-2-trifluoromethylbenzoyl]-5-cyclopropylisoxazole;
13. 5-cyclopropyl-4-[2-methyl-3-(methylsulphenyl)-4-(methylsulphonyl)benzoyl]isoxazole;
14. 4-[3,4-bis(methylsulphonyl)2-methylbenzoyl]-5-cyclopropylisoxazole;
15. 5-cyclopropyl-4-[2-methyl-3-(methylsulphenyl)-4-(methylsulphonyl)benzoyl]isoxazole;
16. ethyl 4-[2,3-bis(methylsulphenyl)-4-chlorobenzoyl]-5-cyclopropylisoxazole-3-carboxylate;
17. 4-[4-chloro-3-(ethylsulphenyl)-2-(methylsulphenyl)benzoyl]-5-cyclopropylisoxazole;
18. 4-[4-chloro-3-(choromethylsulphenyl)-2-methoxybenzoyl]-5-cyclopropylisoxazole;
19. 4-[4-chloro-3-(choromethylsulphenyl)-2-methoxybenzoyl]-5-cyclopropylisoxazole;
20. 4-[4-chloro-3-(chloromethylsulphenyl)-2-methoxybenzoyl]-5-cyclopropylisoxazole;
21. 4-[4-chloro-2-(methylsulphenyl)-3-(propylsulphenyl)benzoyl]-5-cyclopropylisoxazole;
22. 4-[4-chloro-3-(1-methylethylsulphenyl)-2-(methylsulphenyl)benzoyl]-5-cyclopropylisoxazole.

The numbers 1 to 22 are assigned to these compounds for reference and identification hereafter.

Compounds of formula (I) may be prepared by the application or adaptation of known methods (i.e. methods heretofore used or described in the literature), for example as hereinafter described.

In the following description where symbols appearing in formulae are not specifically defined, it is to be understood that they are "as hereinbefore defined" in accordance with the first definition of each symbol in the specification.

It is to be understood that in the descriptions of the following processes the sequences may be performed in different orders, and that suitable protecting groups may be required to achieve the compounds sought.

According to a feature of the present invention compounds of formula (I) in which R represents hydrogen may be prepared by the reaction of a compound of formula (II):

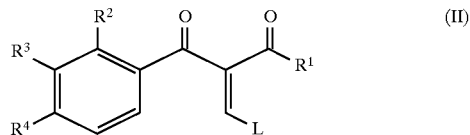

wherein L is a leaving group and R$^1$, R$^2$, R$^3$ and R$^4$ are as hereinbefore defined, with hydroxylamine or a salt of hydroxylamine. Hydroxylamine hydrochloride is generally preferred. Generally L is alkoxy, for example ethoxy, or N,N-dialkylamino, for example N,N-dimethylamino. The reaction is generally carried out in an organic solvent such as ethanol or acetonitrile or a mixture of a water-miscible organic solvent and water, preferably in a ratio of organic solvent: water of from 1:99 to 99:1, optionally in the presence of a base or acid acceptor such as triethylamine or sodium acetate at a temperature from 0° to 100° C.

According to a further feature of the present invention compounds of formula (I) in which R represents hydrogen may be prepared by the reaction of a compound of formula (III):

wherein R$^1$ is as hereinbefore defined and Y represents a carboxy group or a reactive derivative thereof (such as a carboxylic acid chloride or carboxylic ester), or a cyano group, with an appropriate organometallic reagent such as a Grignard reagent or an organolithium reagent. The reaction is generally carried out in an inert solvent such as ether or tetrahydrofuran at a temperature from 0° C. to the reflux temperature of the mixture.

According to a further feature of the present invention compounds of formula (I) wherein R represents a group —CO$_2$R$^5$, n represents 0 or 2, R$^2$ represents a group R$^{21}$ which is as hereinbefore defined for R$^2$ provided that p is 0 or 2, and R$^4$ represents a group R$^{41}$ which is as hereinbefore defined for R$^4$ provided that p is 0 or 2, may be prepared by the reaction of a compound of formula (IV)

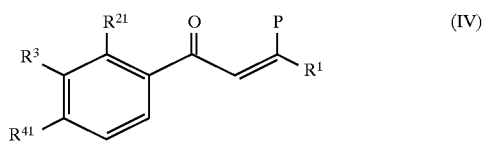

wherein R$^1$, R$^{21}$, R$^3$ and R$^{41}$ are as hereinbefore defined, n is 0 or 2 and P is a leaving group such as N,N-dialkylamino, with a compound of formula R$^5$O$_2$CC(Z)=NOH wherein R$^5$ is as hereinbefore defined and Z is a halogen atom. Generally Z is chlorine or bromine. The reaction is generally performed in an inert solvent such as toluene or dichloromethane either in the presence of a base such as triethylamine or a catalyst such as a 4 Angstrom molecular sieve or fluoride ion.

According to a further feature of the present invention compounds of formula (I) in which R represents a group —$CO_2R^4$, n is 0 or 2, $R^2$ represents $R^{21}$ as hereinbefore defined and $R^4$ represents a group $R^{41}$ as hereinbefore defined, may be prepared by the reaction of a compound of formula (V):

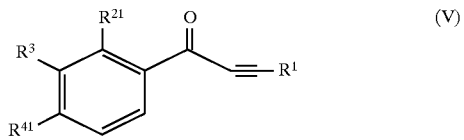

wherein $R^1$, $R^{21}$, $R^3$ and $R^{41}$ are as hereinbefore defined and n is 0 or 2, with a compound of formula $R^5O_2CC(Z)=NOH$ wherein Z and $R^5$ are as hereinbefore defined. The reaction is generally performed in an inert solvent such as toluene or dichloromethane optionally in the presence of a base such as triethylamine or a catalyst such as a 4 Angstrom molecular sieve or fluoride ion. The reaction can be carried out at a temperature between room temperature and the reflux temperature of the mixture.

According to a further feature of the present invention compounds of formula (I) wherein R represents —$COR^5$, n is 0 or 2, $R^2$ represents $R^{21}$ as hereinbefore defined and $R^4$ represents $R^{41}$ as hereinbefore defined, may be prepared by the reaction of a salt of a compound of formula (VI):

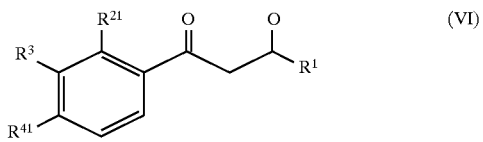

wherein $R^1$, $R^{21}$, $R^3$ and $R^{41}$ are as hereinbefore defined and n is 0 or 2, with a compound of formula $R^5O_2CC(Z)=NOH$ wherein $R^5$ and Z are as hereinbefore defined. Preferred salts include sodium or magnesium salts. The reaction may be performed in an inert solvent such as dichloromethane or acetonitrile at a temperature between room temperature and the reflux temperature of the mixture.

Intermediates in the preparation of compounds of formula (I) may be prepared by the application or adaptation of known methods.

Compounds of formula (II) may be prepared by the reaction of compounds of formula (VI) with either a trialkyl orthoformate such as triethyl orthoformate or a dimethylformamide dialkl acetal such as dimethylformamide dimethyl acetal.

The reaction with triethyl orthoformate can be carried out in the presence of acetic anhydride at the reflux temperature of the mixture and the reaction with dimethylformamide dialkyl acetal is carried out optionally in the presence of an inert solvent at a temperature from room temperature to the reflux temperature of the mixture.

Compounds of formula (IV) may be prepared by the reaction of a compound of formula (VII) with a benzoyl chloride of formula (VIII):

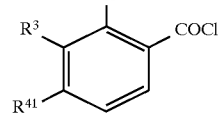

wherein $R^1$, $R^{21}$, $R^3$, $R^{41}$ and P are as hereinbefore defined and n is 0 or 2. The reaction is generally carried out in the presence of an organic base such as triethylamine in an inert solvent such as toluene or dichloromethane at a temperature between −20° C. and room temperature.

Compounds of formula (V) may be prepared by the metallation of an acetylene of formula (IX):

wherein $R^1$ is as hereinbefore defined, followed by reaction of the metal salt thus obtained with a benzoyl chloride of formula (VIII). The metallation is generally performed using n-butyl lithium in an inert solvent such as ether or tetrahydrofuran at a temperature from −78° C. to 0° C. The subsequent reaction with the benzoyl chloride is carried out in the same solvent at a temperature between −78° C. and room temperature.

Compounds of formula (VI) may be prepared by the reaction of an acid chloride of formula (VIII) with the metal salt of a compound of formula (X);

wherein $R^1$ is as hereinbefore defined, to give a compound of formula (XI):

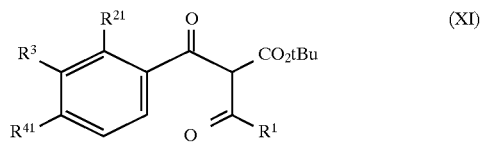

wherein $R^1$, $R^{21}$ $R^3$, and $R^{41}$ are as hereinbefore defined and n is 0 or 2, which is subsequently decarboxylated to give a compound of formula (VI). The reaction to produce the metal salt of a compound of formula (X) is generally performed in a solvent such as a lower alcohol, preferably methanol. Preferably the metal is magnesium. The metal salt of the compound of formula (X) is subsequently reacted with an acid chloride of formula (VIII) in an inert solvent such as toluene or acetonitrile. The decarboxylation is generally performed by refluxing the compound of formula (XI) in the presence of a catalyst, such as paratoluenesulphonic acid, in an inert solvent e.g. toluene.

Acid chlorides of formula (VIII) may be prepared by the reaction of a benzoic acid of formula (XII):

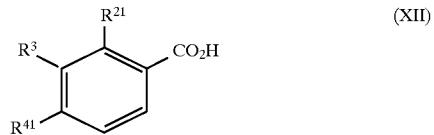

wherein $R^{21}$, $R^3$ and $R^{41}$ are as hereinbefore defined and n is 0 or 2, with a chlorinating agent, for example thionyl chloride at the reflux temperature of the mixture.

Intermediates of formulae (III), (VII), (IX), (X) and (XII) are known or may be prepared by the application or adaptation of known methods.

Those skilled in the art will appreciate that some compounds of formula (I) may be prepared by the interconversion of other compounds of formula (I) and such interconversions constitute yet more features of the present invention. Examples of such interconversions are hereafter described.

According to a further feature of the present invention compounds in which p is one or two and/or q is one or two may be prepared by the oxidation of the sulphur atom of the corresponding compounds in which p and/or q is zero or one. The oxidation of the sulphur atom is generally carried out using for example 3-chloroperoxybenzoic acid in an inert solvent such as dichloromethane at a temperature from −40° C. to room temperature.

The following examples illustrate the preparation of compounds of formula (I) and the following reference examples illustrate the preparation of intermediates of the invention. In the present specification b.p. means boiling point; m.p. means melting point; cPr represents cyclopropyl.

EXAMPLE 1

Sodium acetate (1.31 g) was added to a mixture of 1-[2,3-bis(methylsulphenyl)-4-chlorophenyl]-3-cyclopropyl-2-ethoxymethylenepropan-1,3-dione (4.1 g) and hydroxylamine hydrochloride (1.11 g) in ethanol and the mixture was stirred at room temperature overnight. The mixture was poured into water and the resultant solid was filtered off, triturated with ethanol and filtered to eve 4-[2,3-bis(methylsulphenyl)-4-chlorobenzoyl]-5-cyclopropylisoxazole (compound 1. 2.48 g) as an off-white solid m.p. 130.5°–131.5° C.

By proceeding in a similar manner the following compounds of formula (I) were prepared from the appropriately substituted starting materials.

| Cpd | R | $R^1$ | $R^2$ | $R^3$ | $R^4$ | m.p./NMR |
|-----|---|-------|-------|-------|-------|----------|
| 2   | H | cPr | $SO_2Me$ | SMe | Cl | 145–147° C. |
| 3   | H | cPr | Cl | $SO_2Me$ | Cl | 119–122° C. |
| 4   | H | cPr | $CF_3$ | SMe | SMe | 96–97° C. |
| 5   | H | cPr | $CF_3$ | SMe | $SO_2Me$ | 128–130° C. |
| 7   | H | cPr | $CF_3$ | SMe | Cl | 91–93° C. |
| 8   | H | cPr | $SO_2Me$ | $SCH_2CH=CH_2$ | Cl | 122–124° C. |
| 9   | H | cPr | $SO_2Me$ | SMe | Br | 140–142° C. |
| 10  | H | cPr | SMe | SMe | Br | 116–118° C. |
| 13  | H | cPr | Me | SMe | $SO_2Me$ | a |
| 17  | H | cPr | SMe | SEt | Cl | 105–106° C. |
| 21  | H | cPr | SMe | SPr | Cl | 67–69° C. |
| 22  | H | cPr | SMe | SisoPr | Cl | 105–106° C. | a NMR(CDCl$_3$) 1.2–1.3(m,2H), 1.35–1.4(m,2H), 2.4(s,3H), 2.5–2.55(m,1H), 2.6(s,3H), 3.45(s,3H), 7.4(d,1H), 8.1(s,1H), 8.15(d.1H).

EXAMPLE 2

Hydrogen peroxide (30%, 1.3 ml) was added to a solution of 4-[3,4-bis(methylsulphenyl)-2-trifluoromethylbenzoyl]-5-cyclopropylisoxazole(1.0 g) in a mixture of acetic acid and acetic anhydride and the mixture was stirred and heated at 70° C. for 1 hour. Further acetic anhydride and hydrogen peroxide (2.0 ml) was added and the mixture was heated at 70° C. for 3 hours. It was cooled and poured into water. The solid was filtered off and washed with aqueous sodium bisulphite solution and water to give 4-[3,4-bis(methylsulphonyl)-2-trifluoromethylbenzoyl]-5-cyclopropylisoxazole (compound 6, 0.85 g) as a white solid, m.p. 222°–223° C.

By proceeding in a similar manner the following compound was prepared from the appropriately substituted starting material.

4-[3,4-Bis(methylsulphonyl)-2-methylbenzoyl]-5-cyclopropylisoxazole (compound 14), m.p. 191°–193° C. from 5-cyclopropyl-4-[2-methyl-3-(methylsulphenyl)-4-(methylsulphonyl)-benzoyl]isoxazole.

EXAMPLE 3

3-Chloroperoxybenzoic acid (50%, 2.7 g) was added to a stirred, cooled solution of 4-[4-chloro-3-(methylsulphenyl) -2-trifluoromethylbenzoyl]-5-cyclopropylisoxazole (1.5 g) in dichloromethane at 0° C. The mixture was stirred at 0° C. for 1 hour and at room temperature overnight. It was washed with aqueous sodium metabisulphite solution, then quickly with aqueous sodium bicarbonate solution and water, dried (Na$_2$SO$_4$) and filtered. The filtrate was evaporated to dryness and the residue was separated into the two main components by chromatography to give 4-[4-chloro-3-(methylsulphonyl) -2-trifluoromethylbenzoyl]-5-cyclopropylisoxazole (compound 11, 0.86 g) as a white solid, m.p. 139.5°–141° C. and 4-[4-chloro-3-(methylsulphinyl)-2-trifluoromethylbenzoyl]-5-cyclopropylisoxazole (compound 12, 0.28 g) as a white solid, m.p. 122°–124° C.

By proceeding in a similar manner the following compounds were prepared from the appropriately substituted starting material.

5-Cyclopropyl-4-[2-methyl-3-(methylsulphinyl)-4-(methylsulphonyl)benzoyl]isoxazole (compound 15), m.p. 153°–154.5° C. from 5-cyclopropyl-4-[2-methyl-3-(methylsulphenyl)-4-(methylsulphonyl)benzoyl]isoxazole.

4-[4-Chloro-3-(chloromethylsulphinyl)-2-methoxybenzoyl]-5-cyclopropylisoxazole (compound 19) as a clear gum, NMR (CDCl$_3$ 1.2–1.4(m,4H), 3.9(s,3H), 4.9(d,1H), 5.2(d,1H), 7.4(d,1H), 7.6(d,1H), 8.2(s,1H) from 4-[4-chloro-3-(chloromethylsulphenyl)-2-methoxybenzoyl] -5-cyclopropylisoxazole.

4-[4-Chloro-3-(chloromethylsulphonyl)-2-methoxybenzoyl]-5-cyclopropylisoxazole (compound 20) as a white solid, m.p. 118.9°–119.8° C. from 4-[4-chloro-3-(chloromethylsulphenyl)-2-methoxybenzoyl]-5-cyclopropylisoxazole.

EXAMPLE 4

A mixture of magnesium (0.27 g) and methanol containing carbon tetrachloride (0.1 ml) was heated at reflux for 0.5 hours. It was cooled and 1-[2,3-bis(methylsulphenyl)-4-chlorophenyl]-3-cyclopropylpropan-1,3-dione (3.4 g) was added. The resultant mixture was stirred and heated at reflux for 2 hours. It was cooled and evaporated to dryness. The residue was dissolved in dichloromethane and a solution of ethyl chloro-oximidoacetate (1.82 g) in dichloromethane was added. The mixture was stirred at room temperature overnight. Hydrochloric acid (2M) was added and the mixture was stirred for 0.5 hours. The layers were separated and the organic phase was washed with water, dried (Na$_2$SO$_4$) and filtered. The filtrate was evaporated to dryness and the residue was purified by chromatography eluted with the mixture of ethyl acetate and hexane (1:9) to give ethyl 4-[2,3-bis(methylsulphenyl)-4-chlorobenzoyl]-5-cyclopropylisoxazole-3-carboxylate (compound 16, 3.02 g) as an orange oil, NMR (CDCl$_3$) 1.1 (m,2H), 1.15(t,3H), 1.3(m,2H), 2.25(m,1H), 2.35(s,3H), 2.4(s,3H), 4.1(q,2H), 7.2(d,1H), 7.45(d,1H).

EXAMPLE 5

A crude mixture containing 1-[4-chloro-3-(chloromethylsulphenyl)-2-methoxyphenyl]-3-cyclopropyl-2-ethoxymethylenepropan-1,3-dione and 1-[4-chloro-2-methoxy-3-(methylsulphenyl)phenyl]-3-cyclopropyl-2-ethoxymethylenepropan-1,3-dione (approx 1:2, 25.1 g) was dissolved in ethanol and hydroxylamine hydrochloride (6.03 g) was added, followed by sodium acetate (5.25 g). The mixture was stirred at room temperature overnight then evaporated to dryness. The residue was dissolved in ethyl acetate and washed with water, dried (MgSO$_4$) and filtered. The filtrate was evaporated to dryness to give a crude mixture of 4-[4-chloro-3-(chloromethylsulphenyl)-2-methoxybenzoyl]-5-cyclopropylisoxazole and 4-[4-chloro-2-methoxy-3-(methylsulphenyl)benzoyl]-5-cyclopropylisoxazole which was purified by column chromatography eluted with a mixture of ethyl acetate and hexane (1:20) from which the only product isolated pure was 4-[4-chloro-3-(chloromethylsulphenyl)-2-methoxybenzoyl]-5-cyclopropylisoxazole (compound 18, 4.01 g) m.p. 70°–71.6° C., NMR (CDCl$_3$) 1.2–1.4(m,4H), 2.65–2.8(m, 1H), 3.8(s,3H), 5.05(s,2H), 7.4(s,2H), 8.25(s,1H).

REFERENCE EXAMPLE 1

A mixture of 1-[2,3-bis(methylsulphenyl)-4-chlorophenyl]-3-cyclopropylpropan-1,3-dione (3.45 g) and acetic anhydride (3.37 g) in acetic acid was stirred and heated at reflux for 3 hours. It was cooled and evaporated to dryness. The residue was dissolved in toluene and re-evaporated to give 1-[2,3-bis(methylsulphenyl)4-chlorophenyl]-3-cyclopropyl-2-ethoxymethylenepropan-1,3-dione (4.1g) as a brown oil which was not further purified.

By proceeding in a similar manner the following compounds were prepared from the appropriately substituted starting materials;

| R$^1$ | R$^2$ | R$^3$ | R$^4$ |
|---|---|---|---|
| cPr | SO$_2$Me | SMe | Cl |
| cPr | Cl | SO$_2$Me | Cl |
| cPr | CF$_3$ | SMe | SMe |
| cPr | CF$_3$ | SMe | SO$_2$Me |
| cPr | CF$_3$ | SMe | Cl |
| cPr | SO$_2$Me | SCH$_2$CH=CH$_2$ | Cl |
| cPr | SO$_2$Me | SMe | Br |
| cPr | SMe | SMe | Br |
| cPr | Me | SMe | SO$_2$Me |
| cPr | SMe | SEt | Cl |
| cPr | SMe | SPr | Cl |
| cPr | SMe | SisoPr | Cl |

REFERENCE EXAMPLE 2

A mixture of magnesium (0.44 g) and methanol containing carbon tetrachloride (0.1 ml) was heated at reflux for half an hour. t-Butyl 3-cyclopropyl-3-oxopropionate (3.0 g) was added dropwise and the resultant suspension was heated at reflux for 1 hour. It was cooled and evaporated to dryness. Toluene was added and the mixture was re-evaporated to dryness. The residue was dissolved in toluene and 2,3-bis(methylsulphenyl)-4-chlorobenzoyl chloride (4.35 g) was added. The mixture was stirred at room temperature overnight. Hydrochloric acid (2M) was added and the mixture was stirred for half an hour. The layers were separated and the organic layer was washed with water and dried by azeotropic removal of water using a Dean & Stark apparatus. 4-Toluenesulphonic acid (0.1 g) was added and the mixture was heated at reflux for 2 hours. It was cooled, washed with water, dried (Na$_2$SO$_4$) and filtered. The filtrate was evaporated to dryness and the residue was purified by chromatography eluted with a mixture of ethyl acetate and n-hexane to give 1-[2,3-bis(methylsulphenyl)-4-chlorophenyl]-3-cyclopropylpropan-1,3-dione (3.45 g) as an orange oil NMR (CDCl$_3$) 0.9–1.1(m,2H), 1.2–1.3(m,2H), 1.7–1.8(m, 1H), 2.45(s,3H), 2.48(s,3H), 6.0(s,1H), 7.3(d,1H) 7.45(d,1H) 15.6–16.0(bs,1H).

By proceeding in a similar manner the following compounds of formula (VI) above were prepared from the appropriately substituted starting materials:

| R$^1$ | R$^{21}$ | R$^3$ | R$^{41}$ | m.p./NMR |
|---|---|---|---|---|
| cPr | SO$_2$Me | SMe | Cl | — |
| cPr | Cl | SO$_2$Me | Cl | Note 1:(a) |
| cPr | CF$_3$ | SMe | SMe | 96–97° C. |
| cPr | CF$_3$ | SMe | SO$_2$Me | (b) |
| cPr | CF$_3$ | SMe | Cl | (c) |
| cPr | SO$_2$Me | SCH$_2$CH=CH$_2$ | Cl | — |
| cPr | SO$_2$Me | SMe | Br | — |
| cPr | SMe | SMe | Br | — |
| cPr | Me | SMe | SO$_2$Me | 144–146° C. |
| cPr | SMe | SEt | Cl | (d) |
| cPr | SMe | SPr | Cl | (e) |
| cPr | SMe | SisoPr | Cl | (f) |

Note 1: Toluene replaced by acetonitrile for first stage.
(a) NMR (CDCl$_3$) 1.0–1.1(m,2H), 1.2–1.3(m,2H), 1.7–1.85 (m,1H), 3.4(s,3H), 5.95(s,1H), 7.6(s,2H), 15.7–16.1(bs, 1H).
(b) NMR (CDCl$_3$) 0.95–1.1(m,2H), 1.2–1.3(m,2H), 1.65–1.75 (m,1H) 2.6(s,3H), 3.5(s,3H), 5.8(s,1H), 7.6(d, 1H), 8.45(d,1H).
(c) NMR (CDCl$_3$) 0.95–1.1(m,2H) 1.2–1.3(m,2H), 1.65–1.75(m,1H), 2.45(s,3H), 5.8(s,1H), 7.35(d,1H), 7.7 (d,1H), 15.4–15.8(bs,1H).
(d) NMR (CDCl$_3$) 0.85–1.0(m,2H), 1.1–1.2(m,2H), 1.2(t, 3H), 1.6–1.7(m,1H), 2.4(s,3H), 2.95(q,2H), 5.9(s,1H), 7.25(d,1H), 7.35(d 1H), 15.7–16.1(bs,1H).
(e) NMR (CDCl$_3$) 0.9–1.1(m,5H), 1.2–1.3(m,2H), 1.6(q, 2H), 1.65–1.8(m,1H), 2.5(s,3H), 2.95(t,2H), 6.0(s,1H), 7.3(d,1H), 7.45(d,1H), 15.7–16.1(bs,1H).
(f) NMR (CDCl$_3$) 0.95–1.1(m,2H), 1.15–1.25(m,2H), 1.3(d, 6H), 1.7–1.8(m,1H), 2.5(s,3H), 3.65(m,1H), 6.05(s,1H), 7.3(d,1H), 7.45(d,1H), 15.7–16.2(bs,1H).

Benzoyl chlorides were prepared by treating the corresponding benzoic acids with thionyl chloride, heating at reflux for 4 hours. The excess thionyl chloride was removed by evaporation, treatment with toluene and re-evaporation. The residual benzoyl chlorides were used without further purification.

REFERENCE EXAMPLE 3

Lithium hydroxide monohydrate (4.95 g) was added to a solution of methyl mercaptan (4.4 g) in N,N-dimethyl formamide, and 4-chloro-3-fluoro-2-(methylsulphenyl) benzoic acid (5.5 g) was added to the resultant mixture. It was stirred at room temperature for 1 hour and heated to 80° C. overnight. It was cooled, poured into water, extracted with ether, washed with water, dried (Na$_2$SO$_4$) and filtered. The filtrate was evaporated to dryness and the residue was purified by column chromatography eluted with a mixture of acetic acid, ether and hexane (1:10:89) to give 2,3-bis(methylsulphenyl)-4-chlorobenzoic acid (3.24 g) as an off white solid, m.p. 130°–131° C.

By proceeding in a similar manner the following compounds were prepared from the appropriately substituted starting material.

3,4-Bis(methylsulphenyl)-2-trifluoromethylbenzoic acid, NMR(CDCl$_3$) 2.35(s,3H), 2.4(s,3H), 4.7–5.4(bs, 1H), 7.2(d, 1H), 7.5(d,1H).

2,3-Bis(methylsulphenyl)-4-bromobenzoic acid, m.p. 99°–101° C.

4-Chloro-3-(ethylsulphenyl)-2-(methylsulphenyl)benzoic acid, NMR (CDCl$_3$) 1.25(t,3H), 2.55(s,3H), 3.0(q,2H), 7.55 (d,1H), 7.9(d, 1H).

4-Chloro-2-(methylsulphenyl)-3-(propylsulphenyl) benzoic acid, m.p. 92°–3° C.

4-Chloro-3-(1-methylethylsulphenyl)-2-(methylsulphenyl)benzoic acid, NMR (CDCl$_3$) 1.3(d,6H), 2.55(s,3H), 3.65(m,1H), 7.55(d,1H), 7.9(d,1H).

REFERENCE EXAMPLE 4 n-Butylithium (2.5M in hexane, 180 ml) was added dropwise to a stirred, cooled solution of 4-chloro-3-fluorobenzoic acid (37.5 g) in tetrahydrofuran while maintaining the temperature below −40° C. The mixture was stirred at −40° C. for 3 hours. Dimethyl disulphide (60.5 g) in tetrahydrofuran was added dropwise and the mixture was stirred at −40° C. for half an hour and at room temperature overnight. Hydrochloric acid (2M) was added and the layers were separated. The aqueous layer was extracted with ether and the combined organic layers were extracted with aqueous sodium hydroxide (2M). The aqueous extract was acidified to pH1 and extracted with ether. washed with water, dried (Na$_2$SO$_4$) and filtered. The filtrate was evaporated to dryness and the residue was triturated with n-hexane and filtered to give 4-chloro-3-fluoro-2-(methylsulphenyl) benzoic acid (32.84 g) as a white solid m.p. 149.5°–150.50° C.

REFERENCE EXAMPLE 5

Lithium hydroxide monohydrate (1.26 g) was added to a solution of methyl mercaptan (0.72 g) in dimethyl formamide. To this mixture was added 4-chloro-3-fluoro-2-(methylsulphonyl)benzoic acid (3.7 g). The mixture was stirred for 2 hours then poured into water and acidified to pH1. It was extracted with ether, washed with water, dried (Na$_2$SO$_4$) and filtered. The filtrate was evaporated to dryness and the residue was triturated with n-hexane and filtered to give 4-chloro-3-(methylsulphenyl)-2-(methylsulphonyl) benzoic acid (2.26 g) as a white solid, NMR (CDCl$_3$) 2.5(s,3H), 3.45(s,3H), 7.5(d,1H), 7.7(d,1H).

By proceeding in a similar manner the following compounds were prepared from the appropriately substituted starting materials.

3-(Methylsulphenyl)-4-(methylsulphonyl)-2-trifluoromethylbenzoic acid, NMR (CDCl$_3$) 2.2(s,3H), 3.2 (s,3H), 7.4(d,1H), 8.1(d,1H).

4-Chloro-3-(methylsulphenyl)-2-trifluoromethylbenzoic acid, NMR (CDCl$_3$) 2.45(s,3H), 5.2–5.8(bs,1H), 7.5(d,1H), 7.7(d,1H).

4-Chloro-2-(methylsulphonyl)-3-(prop-2-enylsulphenyl) benzoic acid, NMR (CDCl$_3$) 3.5(s,3H), 3.7(d,2H), 5.1(dd, 2H), 5.9(m,1H), 7.5(d,1H), 7.8(d,1H).

4-Bromo-3-(methylsulphenyl)-2-(methylsulphonyl) benzoic acid, m.p. 174°–176° C.

2-Methyl-3-(methylsulphenyl)-4-(methylsulphonyl) benzoic acid, m.p. 116°–117° C.

REFERENCE EXAMPLE 6

Hydrogen peroxide (30%; 30 ml) was added to a stirred suspension of 4-chloro-3-fluoro-2-(methylsulphenyl) benzoic acid (18.39 g) in glacial acetic acid containing concentrated sulphuric acid (1 ml). The mixture was stirred for 1 hour then heated gradually to 90° C. and at that temperature for 3 hours. It was cooled and left to stand overnight then poured into water and stirred for a quarter of an hour. The precipitated solid was filtered off to give 4-chloro-3-fluoro-2-(methylsulphonyl)benzoic acid (12.25 g) as a white solid, m.p. 207.5°–209° C.

By proceeding in a similar manner the following compounds were prepared from the appropriately substituted starting materials 2,4-Dichloro-3-(methylsulphonyl)toluene. m.p. 84°–85.5° C.

REFERENCE EXAMPLE 7

Potassium permanganate (33.66 g) was added in portions to a stirred heated suspension of 2,4-dichloro-3-(methylsulphonyl)toluene (16.88 g) in water at 95°–100° C. The mixture was stirred and heated at reflux for one and a half hours. The hot suspension was filtered and the filtrate was cooled to 0° C. and acidified. It was filtered to give 2,4-dichloro-3-(methylsulphonyl)benzoic acid (5.35 g) as an orange solid, m.p. 157.5°–158.5° C.

REFERENCE EXAMPLE 8

A solution of sodium nitrite (12.0 g) in water was added to a stirred suspension of 2,6-dichloro-3-methylaniline (30.0 g) in a mixture of glacial acetic acid and concentrated hydrochloric acid. While maintaining the temperature below 10° C. The mixture was stirred at 0° C. for three quarters of an hour then added to a mixture of dimethyl disulphide (20 ml) and copper powder (0.25 g) in glacial acetic acid. The mixture was stirred for 4 hours and extracted with ether. The organic layer was washed with aqueous sodium carbonate (2M), water, dried (Na$_2$SO$_4$) and filtered. The filtrate was evaporated to dryness to give 2,4-dichloro-3-(methylsulphenyl)toluene (27.2 g) as a red liquid NMR (CDCl$_3$) 2.4(s,3H), 2.45(s,3H), 7.15(d,1H), 7.3(d,1H).

REFERENCE EXAMPLE 9 n-Butylithium (2.5M in hexane, 51 ml) was added to a stirred, cooled solution of 6-bromo-2-fluoro-3-(methylsulphenyl)benzotrifluoride (30.6 g) in ether while maintaining the temperature below −70° C. The mixture was stirred at −78° C. for 4 hours and then poured onto carbon dioxide pellets. It was stirred for 2 hours and diluted with water. It was washed with ether and the aqueous layer was acidified and extracted with ether, washed with water, dried (MgSO$_4$) and filtered. The filtrate was evaporated to dryness to give 3-fluoro-4-(methylsulphenyl)-2-trifluoromethylbenzoic acid (23.4 g) as a beige solid. NMR (DMSO-d$_6$) 3.14(s,3H), 7.99(d,1H), 8.19(t,1H).

By proceeding in a similar manner 4-chloro-3-fluoro-2-trifluoromethylbenzoic acid was prepared from the appropriately substituted starting materials. m.p. 108°–109° C.

REFERENCE EXAMPLE 10

A solution of sodium nitrite (11.2 g) in concentrated sulphuric acid was added to a stirred cooled suspension of 4-bromo-2-fluoro-3-trifluoromethylaniline (40 g) in glacial acetic acid while maintaining the temperature below 5° C. The mixture was stirred at 5° C. for one and a half hours. The resultant mixture was added gradually to a mixture of dimethyl disulphide (20 ml) and copper power (0.224 g) in glacial acetic acid at 45° C. It was stirred and heated at 70° C. for 3 hours. It was cooled, poured into water, extracted with ether, washed with water, dried (MgSO$_4$) and filtered. The filtrate was evaporated to dryness and purified by column chromatography eluted with petroleum spirit (b.p.

60°–80° C.) to give 6-bromo-2-fluoro-3-(methylsulphenyl) benzotrifluoride (30.6 g) as an orange oil NMR (CDCl$_3$) 2.45(s,3H), 7.25(t,1H), 7.5(d,1H).

REFERENCE EXAMPLE 11

A solution of N-bromosuccinimide (24.9 g) in N,N-dimethyl formamide was added to a solution of 2-fluoro-3-trifluoromethylaniline (25 g) in dimethyl formamide. The mixture was stirred for four and a half hours. It was poured into water and the oil was separated. The aqueous layers was extracted with ether and the combined organic layers were washed with water, dried (MgSO$_4$) and filtered. The filtrate was evaporated to dryness and the residue was distilled to give 4-bromo-2-fluoro-3-trifluoromethylaniline (27.44 g) as an orange oil, b.p. 88°–94° C./4 mbar.

REFERENCE EXAMPLE 12

Hydrogen peroxide (30%, 19 ml) was added dropwise to a solution of 3-fluoro-4-(methylsulphenyl)-2-trifluoromethylbenzoic acid (5.0 g) in a mixture of acetic acid and acetic anhydride. The mixture was stirred for 1 hour and heated at 70° C. for 4 hours. It was cooled, poured into water and extracted with ethyl acetate. The organic extract was washed with aqueous sodium metabisulphite solution, water, aqueous ferrous sulphate solution, water, dried (MgSO$_4$) and filtered. The filtrate was evaporated to dryness to give 3-fluoro-4-(methylsulphonyl)-2-trifluoromethylbenzoic acid (0.8 g). The aqueous layers were combined and evaporated to dryness and the residue was suspended in ethyl acetate and heated at reflux for half an hour. The hot ethyl acetate solution was decanted off and washed with saturated sodium chloride solution, dried (MgSO$_4$) and filtered. The filtrate was evaporated to dryness to give 3-fluoro-4-(methylsulphonyl)-2-trifluoromethylbenzoic acid (4.0 g) as a beige solid, NMR (CDCl$_3$+CD$_3$CN) 3.15(s,3H), 7.45(d,1H), 8.05(t,1H).

By proceeding in a similar manner 4-bromo-3-fluoro-2-(methylsulphonyl)benzoic acid was prepared from the appropriately substituted starting materials, m.p. 250°–252° C.

REFERENCE EXAMPLE 13

A solution of sodium nitrite (7.3 g) in concentrated sulphuric acid was added to a stirred cooled solution of 4-bromo-2-fluoro-3-trifluoromethylaniline (27.4 g) in glacial acetic acid while maintaining the temperature below 15° C. The mixture was stirred at 10°–15° C. for one and a half hours then poured into a mixture of copper (I) chloride (10.5 g) in hydrochloric acid (5M). The mixture was stirred for one and a half hours then diluted with water, extracted with ether, washed with aqueous sodium hydroxide solution (2M), water, dried (MgSO$_4$) and filtered. The filtrate was evaporated to dryness and the residue was distilled to give 6-bromo-3-chloro-2-fluorobenzotrifluoride (8.3 g) as a yellow oil b.p. 44°–45° C./2 mbar.

REFERENCE EXAMPLE 14 n-Butyllithium (2.5M in hexane, 63 ml) was added to a solution of diisopropylamine in dry tetrahydrofuran while maintaining the temperature at 0° C. Once addition was complete the cooling bath was removed and the mixture stirred for 30 minutes at room temperature. The resulting solution of lithium di-isopropylamide (LDA) was then added to a solution of 4-bromo-3-fluorobenzoic acid (14.6 g) in tetrahydrofuran while maintaining the temperature at −50° C. The mixture was then stirred for 5 hours at −30° C. A solution of dimethyl disulphide (21 g) in tetrahydrofuran was then added and the cooling bath was removed and the mixture allowed to stir at room temperature overnight. The mixture was diluted with ether and washed with water. The aqueous layer was acidified to pH1 with 2M hydrochloric acid and extracted with ether, washed with water, dried (MgSO$_4$) and filtered. The filtrate was evaporated to dryness and the residue triturated with petroleum spirit (b.p. 60°–80° C.) to give 4-bromo-3-fluoro-2-(methylsulphenyl)benzoic acid (14 g) as a white solid, m.p. 152°–154° C.

REFERENCE EXAMPLE 15

A solution of 4-bromo-3-fluorotoluene (35 g) and sodium hydroxide (7.7 g) in pyridine and water was stirred and heated to reflux. Potassium permanganate (123 g) was added to the mixture over 2 hours. The resulting suspension was heated at reflux for a further 3 hours. The mixture was filtered hot through hyflo silica. The silica was washed with boiling water, followed by ethyl acetate. The cooled aqueous layer was acidified to pH1 with concentrated hydrochloric acid and extracted with ethyl acetate. The organic extract was washed with water, dried (MgSO$_4$) and filtered. The filtrate was evaporated to dryness and the residue triturated with petroleum spirit (b.p. 60°–80° C.) to give 4-bromo-3-fluorobenzoic acid as a white solid (21.25 g), m.p. 213°–215° C.

REFERENCE EXAMPLE 16

A crude mixture containing 1-[4-chloro-3-(chloromethylsulphenyl)-2-methoxyphenyl]-3-cyclopropylpropan-1,3-dione and 1-[4-chloro-2-methoxy-3-(methylsulphenyl)phenyl]-3-cyclopropylpropan-1,3-dione (approx. 1:2, 20g) in acetic anhydride was treated with triethyl orthoformate (96 g). The mixture was stirred and heated at reflux for 4 hours. It was cooled and evaporated to dryness. Xylene was added and it was re-evaporated to dryness to give a crude 1:2 mixture of 1-[4-chloro-3-(chloromethylsulphenyl)-2-methoxyphenyl]-3-cyclopropyl-2-ethoxymethylenepropan-1,3-dione and 1-[4-chloro-2-methoxy-3-(methylsulphenyl)phenyl]-3-cyclopropyl-2-ethoxymethylenepropan-1,3-dione (25.1 g) as a crude brown oil which was not purified further.

REFERENCE EXAMPLE 17

A solution of 4-chloro-2-methoxy-3-(methylsulphenyl) benzoic acid (14.7 g) in thionyl chloride was stirred and heated at reflux for 5 hours. It was cooled and evaporated to dryness. Toluene was added and it was re-evaporated to give an orange oil.

A mixture of magnesium (2.0 g) and methanol containing carbon tetrachloride (1 ml) was warmed gently for 0.5 hours. t-Butyl 3-cyclopropyl-3-oxopropionate (18.4 g) was added and the mixture was heated at reflux for 0.5 hours. It was evaporated to dryness. The residue was dissolved in toluene and re-evaporated to dryness. The residual white solid was dissolved in toluene and the benzoyl chloride from above was added. The mixture was stirred at room temperature overnight. Hydrochloric acid (2M) was added and the mixture was stirred for 0.5 hours. The layers were separated and the organic phase was dried (MgSO$_4$) and filtered. 4-Toluenesulphonic acid (1 g) was added to the filtrate and the mixture was heated at reflux for 4 hours. It was cooled, washed with water, saturated aqueous sodium bicarbonate, water, dried (MgSO$_4$) and filtered. The filtrate was evaporated to dryness to give a 1:2 mixture of 1-[4-chloro-3-

(choromethylsulphenyl)-2-methoxyphenyl]-3-cyclopropylpropan-1,3-dione and 1-[4-chloro-2-methoxy-3-(methylsulphenyl)phenyl]-3-cyclopropylpropan-1,3-dione (22.1 g) as a brown oil, NMR (CDCl$_3$) 0.95–1.05(m,2H), 1.15–1.3(m,2H), 1.75–1.9(m,1H), 2.5(s,0.9H), 3.9(s,3H), 5.05(s,1.4H), 6.55(s,1H), 7.3(d,0.3H), 7.4(d,0.7H), 7.7(d, 0.3H), 7.75(d,0.7H). This was characterised as a 1:2 mixture of the respective compounds from the ratio of the methylene protons at 5.05 ppm to the methyl protons at 2.5 ppm in the above NMR spectrum.

REFERENCE EXAMPLE 18

A mixture of methyl 4-chloro-2-methoxy-3-(methylsulphenyl)benzoate (85% pure, 16.9 g) and lithium hydroxide monohydrate (3.85 g) in aqueous methanol was stirred at room temperature overnight. The mixture was evaporated then treated with water and acidified to pH1. It was extracted with ethyl acetate, dried (MgSO$_4$) and filtered. The filtrate was evaporated to dryness to give 4-chloro-2-methoxy-3-(methylsulphenyl)benzoic acid (14.7 g) as a white solid m.p. 121.3°–122.7° C. NMR (CDCl$_3$) 2.45(s, 3H), 4.05(s,3H), 7.3(d.1H), 7.95(d,1H) containing only a trace of 4-chloro-3-(choromethylsulphenyl)-2-methoxybenzoic acid (determined by NMR).

REFERENCE EXAMPLE 19

Sodium methoxide (5.6 g) was added to a solution of methyl 4-chloro-2-fluoro-3-(methylsulphenyl)benzoate (85% pure, 19.2 g) in dry tetrahydrofuran and the mixture was stirred at room temperature overnight. Water was added and the mixture was extracted with ether, dried (MgSO$_4$) and filtered. The filtrate was evaporated to dryness to give methyl 4-chloro-2-methoxy-3-(methylsulphenyl)benzoate (17.1 g) as a yellow oil NMR (CDCl$_3$) 2.5(s,3H), 3.95(s,3H), 4.0(s,3H), 7.25(d,1H), 7.65(d, 1H) contaminated with 15% methyl 4-chloro-3-(chloromethylsulphenyl)-2-methoxybenzoate (determined by the ratio of NMR signals).

REFERENCE EXAMPLE 20

A mixture of 4-chloro-2-fluoro-3-(methylsulphenyl)benzoic acid (18.25 g) and thionylchloride was stirred and heated at reflux for 5 hours. It was evaporated to dryness and the residue was dissolved in toluene and re-evaporated. The residue was dissolved in methanol and stirred at room temperature overnight. It was evaporated to dryness and the residue was dissolved in ether and washed with water, saturated aqueous sodium bicarbonate, water, dried (MgSO$_4$), treated with decolourizing charcoal and filtered. The filtrate was evaporated to dryness to give methyl 4-chloro-2-fluoro-3-(methylsulphenyl)benzoate (19.2 g) as a yellow oil NMR (CDCl$_3$) 2.5(s,3H), 3.95(s,3H), 7.3(d,1H), 7.8(t,1H) contaminated with 15% methyl 4-chloro-3-(chloromethylsulphenyl)-2-fluorobenzoate (determined by the ratio of NMR signals).

REFERENCE EXAMPLE 21 n-Butylithium (2.5M in hexane, 140 ml) was added to a stirred, cooled solution of crude 2-chloro-6-fluorothioanisole (60.0 g) in dry tetrahydrofuran while maintaining the temperature below –70° C. The mixture was stirred at –78° C. for 3.5 hours then poured onto solid carbon dioxide pellets. It was stirred and allowed to warm to room temperature. It was evaporated to dryness and the residue was dissolved in water and washed with ether. The aqueous layer was acidified to pH1 and extracted with ether, washed with water, dried (MgSO$_4$) and filtered. The filtrate was evaporated to dryness and the residue was triturated with hexane and filtered to give 4-chloro-2-fluoro-3-(methylsulphenyl)benzoic acid as a white solid, m.p. 183°–185° C.

REFERENCE EXAMPLE 22 n-Butylithium (2.5M in hexane, 129 ml) was added to a solution of 3-fluorochlorobenzene (35 g) in dry tetrahydrofuran while maintaining the temperature below –70° C. The mixture was stirred at –78° C. for 3 hours and dimethyl disulphide (60.65 g) was added. The mixture was allowed to warm to room temperature and stirred overnight. The mixture was evaporated to dryness and the residue was suspended in ether and washed with water, dried (MgSO$_4$) and filtered. The filtrate was evaporated to dryness to give 2-chloro-6-fluorothioanisole (60 g) as a crude yellow oil containing some dimethyl disulphide, NMR (CDCl$_3$) 2.45 (s,3H), 6.95(t,1H), 7.1–7.3(m,2H).

According to a feature of the present invention, there is provided a method for controlling the growth of weeds (i.e. undesired vegetation) at a locus which comprises applying to the locus a herbicidally effective amount of at least one isoxazole derivative of formula (I). For this purpose, the isoxazole derivatives are normally used in the form of herbicidal compositions (i.e. in association with compatible diluents or carriers and/or surface active agents suitable for use in herbicidal compositions), for example as hereinafter described.

The compounds of formula (I) show herbicidal activity against dicotyledonous (i.e. broad-leafed) and monocotyledonous (i.e. grass) weeds by pre- and/or post-emergence application.

By the term "pre-emergence application" is meant application to the soil in which the weed seeds or seedlings are present before emergence of the weeds above the surface of the soil. By the term "post-emergence application" is meant application to the aerial or exposed portions of the weeds which have emerged above the surface of the soil. For example, the compounds of formula (I) may be used to control the growth of:

broad-leafed weeds, for example, *Abutilon theophrasti, Amaranthus retroflexus, Bidens pilosa, Chenopodium album, Galium aparine,* Ipomoea spp. e.g. *Ipomoea purpurea, Sesbania exaltata, Sinapis arvensis, Solanum nigrum* and *Xanthium strumarium,* and grass weeds, for example *Alopecurus mvosuroides, Avena fatua, Digitaria sanguinalis, Echinochloa crus-galli, Sorghum bicolor, Eleusine indica* and Setaria spp, e.a. *Setaria faberii* or *Setaria viridis,* and sedges, for example, *Cyperus esculentus.*

The amounts of compounds of formula (I) applied vary with the nature of the weeds, the compositions used, the time of application, the climatic and edaphic conditions and (when used to control the growth of weeds in crop-growing areas) the nature of the crops. When applied to a crop-growin, area the rate of application should be sufficient to control the growth of weeds without causing substantial permanent damage to the crop. In general, taking these factors into account, application rates between 0.01 kg and 5 kg of active material per hectare give good results. However, it is to be understood that higher or lower application rates may be used, depending upon the particular problem of weed control encountered.

The compounds of formula (I) may be used to control selectively the growth of weeds, for example to control the growth of those species hereinbefore mentioned, by pre- or post-emergence application in a directional or non-directional fashion, e.g. by directional or non-directional spraying, to a locus of weed infestation which is an area used, or to be used, for growing crops, for example cereals, e.g. wheat, barley, oats, maize and rice, soya beans, field and dwarf beans, peas, lucerne, cotton, peanuts, flax, onions, carrots, cabbage, oilseed rape, sunflower, sugar beet, and permanent or sown grassland before or after sowing of the crop or before or after emergence of the crop. For the selective control of weeds at a locus of weed infestation which is an area used, or to be used, for growing of crops, e.g. the crops hereinbefore mentioned, application rates between 0.01 kg and 4.0 kg, and preferably between 0.01 kg and 2.0 kg, of active material per hectare are particularly suitable.

The compounds of formula (I) may also be used to control the growth of weeds, especially those indicated above, by pre- or post-emergence application in established orchards and other tree-growing areas, for example forests, woods and parks, and plantations, e.g. sugar cane, oil palm and rubber plantations. For this purpose they may be applied in a directional or non-directional fashion (e.g. by directional or non-directional spraying) to the weeds or to the soil in which they are expected to appear before or after planting of the trees or plantations at application rates between 0.25 kg and 5.0 kg, and preferably between 0.5 kg and 4.0 kg of active material per hectare.

The compounds of formula (I) may also be used to control the growth of weeds, especially those indicated above, at loci which are not crop-growing areas but in which the control of weeds is nevertheless desirable.

Examples of such non-crop-growing areas include airfields, industrial sites, railways, roadside verges, the verges of rivers, irrigation and other waterways, scrublands and fallow or uncultivated land, in particular where it is desired to control the growth of weeds in order to reduce fire risks. When used for such purposes in which a total herbicidal effect is frequently desired, the active compounds are normally applied at dosage rates higher than those used in crop-growing areas as hereinbefore described. The precise dosage will depend upon the nature of the vegetation treated and the effect sought.

Pre- or post-emergence application, and preferably pre-emergence application, in a directional or non-directional fashion (e.g. by directional or non-directional spraying) at application rates between 1.0 kg and 20.0 kg, and preferably between 5.0 and 10.0 kg, of active material per hectare are particularly suitable for this purpose.

When used to control the growth of weeds by pre-emergence application, the compounds of formula (I) may be incorporated into the soil in which the weeds are expected to emerge. It will be appreciated that when the compounds of formula (I) are used to control the growth of weeds by post-emergence application, i.e. by application to the aerial or exposed portions of emerged weeds, the compounds of formula (I) will also normally come into contact with the soil and may also then exercise a pre-emergence control on later-germinating weeds in the soil.

Where especially prolonged weed control is required, the application of the compounds of formula (I) may be repeated if required.

According to a further feature of the present invention, there are provided compositions suitable for herbicidal use comprising one or more of the isoxazole derivatives of formula (I), in association with and preferably homogeneously dispersed in, one or more compatible agriculturally acceptable diluents or carriers and/or surface active agents [i.e. diluents or carriers and/or surface active agents of the type generally accepted in the art as being suitable for use in herbicidal compositions and which are compatible with compounds of formula (I)]. The term "homogeneously dispersed" is used to include compositions in which the compounds of formula (I) are dissolved in other components. The term "herbicidal compositions" is used in a broad sense to include not only compositions which are ready for use as herbicides but also concentrates which must be diluted before use. Preferably, the compositions contain from 0.05 to 90% by weight of one or more compounds of formula (I).

The herbicidal compositions may contain both a diluent or carrier and surface-active (e.g. wetting, dispersing, or emulsifying) agent. Surface-active agents which may be present in herbicidal compositions of the present invention may be of the ionic or non-ionic types, for example sulphoricinoleates, quaternary ammonium derivatives, products based on condensates of ethylene oxide with alkyl and polyaryl phenols, e.g. nonyl- or octyl-phenols, or carboxylic acid esters of anhydrosorbitols which have been rendered soluble by etherification of the free hydroxy groups by condensation with ethylene oxide, alkali and alkaline earth metal salts of sulphuric acid esters and sulphonic acids such as dinonyl- and dioctyl-sodium sulphonosuccinates and alkali and alkaline earth metal salts of high molecular weight sulphonic acid derivatives such as sodium and calcium lignosulphonates and sodium and calcium alkylbenzene sulphonates.

Suitably, the herbicidal compositions according to the present invention may comprise up to 10% by weight, e.g. from 0.05% to 10% by weight, of surface-active agent but, if desired, herbicidal compositions according to the present invention may comprise higher proportions of surface-active agent for example up to 15% by weight in liquid emulsifiable suspension concentrates and up to 25% by weight in liquid water soluble concentrates.

Examples of suitable solid diluents or carriers are aluminium silicate, talc, calcined magnesia, kieselguhr, tricalcium phosphate, powdered cork. absorbent carbon black and clays such as kaolin and bentonite. The solid compositions (which may take the form of dusts, granules or wettable powders) are preferably prepared by grinding the compounds of formula (I) with solid diluents or by impregnating the solid diluents or carriers with solutions of the compounds of formula (I) in volatile solvents, evaporating the solvents and, if necessary, grinding the products so as to obtain powders. Granular formulations may be prepared by absorbing the compounds of formula (I) (dissolved in suitable solvents which may, if desired, be volatile) onto the solid diluents or carriers in granular form and, if desired, evaporating the solvents, or by granulating compositions in powder form obtained as described above. Solid herbicidal compositions, particularly wettable powders and granules, may contain wetting or dispersing agents (for example of the types described above), which may also when solid, serve as diluents or carriers.

Liquid compositions according to the invention may take the form of aqueous, organic or aqueous-organic solutions, suspensions and emulsions which may incorporate a surface-active agent. Suitable liquid diluents for incorporation in the liquid compositions include water, glycols, tetrahydrofurfuryl alcohol, acetophenone, cyclohexanone, isophorone, toluene, xylene, mineral, animal and vegetable oils and light aromatic and naphthenic fractions of petroleum (and mixtures of these diluents). Surface-active agents, which may be present in the liquid compositions, may be ionic or non-ionic (for example of the types described above) and may, when liquid, also serve as diluents or carriers.

Powders, dispersible granules and liquid compositions in the form of concentrates may be diluted with water or other suitable diluents, for example mineral or vegetable oils, particularly in the case of liquid concentrates in which the diluent or carrier is an oil, to give compositions ready for use.

When desired, liquid compositions of the compound of formula (I) may be used in the form of self-emulsifying concentrates containing the active substances dissolved in the emulsifying agents or in solvents containing emulsifying agents compatible with the active substances the simple addition of water to such concentrates producing compositions ready for use.

Liquid concentrates in which the diluent or carrier is an oil may be used at out further dilution using the electrostatic spray technique.

Herbicidal compositions according to the present invention may also contain, if desired, conventional adjuvants such as adhesives, protective colloids, thickeners, penetrating agents, stabilisers, sequestering agents, anti-caking agents, colouring agents and corrosion inhibitors. These adjuvants may also serve as carriers or diluents.

Unless otherwise specified, the following percentages are by weight. Preferred herbicidal compositions according to the present invention are aqueous suspension concentrates which comprise from 10 to 70% of one or more compounds of formula (I), from 2 to 10% of surface-active agent, from 0.1 to 5% of thickener and from 15 to 87.9% of water;

wettable powders which comprise from 10 to 90% of one or more compounds of formula (I), from 2 to 10% of surface-active agent and from 8 to 88% of solid diluent or carrier;

water soluble or water dispersible powders which comprise from 10 to 90% of one or more compounds of formula (I), from 2 to 40% of sodium carbonate and from 0 to 88% of solid diluent;

liquid water soluble concentrates which comprise from 5 to 50%, e.g. 10 to 30%, of one or more compounds of formula (I), from 5 to 25% of surface-active agent and from 25 to 90%, e.g. 45 to 85%, of water miscible solvent, e.g. dimethylformamide, or a mixture of water-miscible solvent and water;

liquid emulsifiable suspension concentrates which comprise from 10 to 70% of one or more compounds of formula (I), from 5 to 15% of surface-active agent, from 0.1 to 5% of thickener and from 10 to 84.9% of organic solvent;

granules which comprise from 1 to 90%, e.g. 2 to 10% of one or more compounds of formula (I), from 0.5 to 7%, e.g. 0.5 to 2%, of surface-active agent and from 3 to 98.5%, e.g. 88 to 97.5%, of granular carrier and emulsifiable concentrates which comprise 0.05 to 90%, and preferably from 1 to 60% of one or more compounds of formula (I), from 0.01 to 10%, and preferably from 1 to 10%, of surface-active agent and from 9.99 to 99.94%, and preferably from 39 to 98.99%, of organic solvent.

Herbicidal compositions according to the present invention may also comprise the compounds of formula (I) in association with and preferably homogeneously dispersed in one or more other pesticidally active compounds and, if desired, one or more compatible pesticidally acceptable diluents or carriers, surface-active agents and conventional adjuvants as hereinbefore described. Examples of other pesticidally active compounds which may be included in, or used in conjunction with, the herbicidal compositions of the present invention include herbicides, for example to increase the range of weed species controlled for example alachlor [2-chloro-2,6'-diethyl-N-(methoxy-methyl)-acetanilide], atrazine [2-chloro-4-ethylamino-6-isopropylamino-1,3,5-triazine], bromoxynil [3,5-dibromos-4-hydroxybenzonitrile], chlortoluron [N'-(3-chloro-methylphenyl)-N,N-dimethylurea], cyanazine [2-chloro-4-(1-cyano-1-methylethylamino)-6-ethylamino-1,3,5-triazine], 2,4-D [2,4-dichlorophenoxy-acetic acid], dicamba [3,6-dichloro-2-methoxybenzoic acid], difenzoquat [1,2-dimethyl-3,5-diphenylpyrazolium salts], flampropmethyl [methyl N-2-(N-benzoyl-3-chloro-4-fluoroanilino)-propionate], fluometuron [N'-(3-trifluoromethylphenyl)-N,N-dimethylurea], isoproturon [N'-(4-isopropylphenyl)-N,N-dimethyurea], insecticides, e.g. synthetic pyrethroids, e.g. permethrin and cypennethrin, and fungicides, e.g. carbamates, e.g. methyl-N-(1-butyl-carbamoyl-benzlmidazol-2-yl)carbamate, and triazoles e.g. 1-(4-chlorophenoxy)-3,3-dimethyl-1-(1,2,4-triazol-1-yl)-butan-2-one. Pesticidally active compounds and other biologically active materials which may be included in, or used in conjunction with, the herbicidal compositions of the present invention, for example those hereinbefore mentioned, and which are acids, may, if desired, be utilized in the form of conventional derivatives, for example alkali metal and amine salts and esters.

The following Examples illustrate herbicidal compositions according to the present invention:

EXAMPLE C1

A soluble concentrate is formed from:

| | |
|---|---|
| Active ingredient (compound 1) | 20% w/v |
| Potassium hydroxide solution 33% w/v | 10% v/v |
| Tetrahydrofurfuryl alcohol (THFA) | 10% v/v |
| Water | to 100 volumes. | by stirring THFA, active ingredient (compound 1) and 90% volume of water and slowly adding the potassium hydroxide solution until a steady pH 7–8 is obtained then making up to volume with water.

Similar soluble concentrates may be prepared as described above by replacing the isoxazole (compound 1) with other compounds of formula (I).

EXAMPLE C2

A wettable powder is formed from:

| | |
|---|---|
| Active ingredient (compound 1) | 50% w/w |
| Sodium dodecylbenzene sulphonate | 3% w/w |
| Sodium lignosulphate | 5% w/w |
| Sodium formaldehyde alkylnaphthalene sulphonate | 2% w/w |
| Microfine silicon dioxide | 3% w/w and |
| China clay | 37% w/w | by blending the above ingredients together and grinding the mixture in an air jet mill.

Similar wettable powders may be prepared as described above by replacing the isoxazole (compound 1) with other compounds of formula (I).

EXAMPLE C3

| A water soluble powder is formed from: | |
| --- | --- |
| Active ingredient (compound 1) | 50% w/w |
| Sodium dodecylbenzenesulphonate | 1% w/w |
| Microfine silicon dioxide | 2% w/w |
| Sodium bicarbonate | 47% w/w | by mixing the above ingredients and grinding the above mixture in a hammer mill.

Similar water soluble powders may be prepared as described above by replacing the isoxazole (compound 1) with other compounds of formula (I).

The compounds of the invention have been used in herbicidal applications according to the following procedures.

METHOD OF USE OF HERBICIDAL COMPOUNDS:

a) General

Appropriate quantities of the compounds used to treat the plants were dissolved in acetone to give solutions equivalent to application rates of up to 1000 g of compound per hectare (g/ha). These solutions were applied from a standard laboratory herbicide sprayer delivering the equivalent of 290 liters of spray fluid per hectare.

b) Weed control: Pre-emergence

The seeds were sown in 70 mm square, 75 mm deep plastic pots in non-sterile soil. The quantities of seed per pot were as follows:

| | | Approx number of seeds/pot |
| --- | --- | --- |
| | Weed species | |
| 1) | Broad-leafed weeds | |
| | Abutilon theophrasti | 10 |
| | Amaranthus retroflexus | 20 |
| | Galium aparine | 10 |
| | Ipomoea purpurea | 10 |
| | Sinapis arvensis | 15 |
| | Xanthium strumarium | 2. |
| 2) | Grass weeds | |
| | Alopecurus myosuroides | 15 |
| | Avena fatua | 10 |
| | Echinochioa crus-galli | 15 |
| | Setaria viridis | 20. |
| 3) | Sedges | |
| | Cyperus esculentus | 3. |
| | Crop | |
| 1) | Broad-leafed | |
| | Cotton | 3 |
| | Soya | 3. |
| 2) | Grass | |
| | Maize | 2 |
| | Rice | 6 |
| | Wheat | 6. |

The compounds of the invention were applied to the soil surface, containing the seeds, as described in (a). A single pot of each crop and each weed was allocated to each treatment, with unsprayed controls and controls sprayed with acetone alone.

After treatment the pots were placed on capillary matting kept in a Lass house and watered overhead. Visual assessment of crop damage was made 20–24 days after spraying. The results were expressed as the percentage reduction in growth or damage to the crop or weeds in comparison with the plants in the control pots.

c) Weed control Post-emergence

The weeds and crops were sown directly into John Innes potting compost in 75 mm deep, 70 mm square pots except for Arnaranthus which was pricked out at the seedling stage and transferred to the pots one week before spraying. The plants were then grown in the greenhouse until ready for spraying with the compounds used to treat the plants. The number of plants per pot were as follows:

| | | Number of Plants per pot | Growth stage |
| --- | --- | --- | --- |
| 1) | Broad leafed weeds | | |
| | Weed species | | |
| | Abutilon theophrasti | 3 | 1–2 leaves |
| | Amaranthus retroflexus | 4 | 1–2 leaves |
| | Galium aparine | 3 | $1^{st}$ whorl |
| | Ipomoea purpurea | 3 | 1–2 leaves |
| | Sinapis arvensis | 4 | 2 leaves |
| | Xanthium strumarium | 1 | 2–3 leaves. |
| 2) | Grass weeds | | |
| | Weed species | | |
| | Alopecurus myosuroides | 8–12 | 1–2 leaves |
| | Avena fatua | 12–18 | 1–2 leaves |
| | Echinochloa crus-galli | 4 | 2–3 leaves |
| | Setaria viridis | 15–25 | 1–2 leaves. |
| 3) | Sedges | | |
| | Weed species | | |
| | Cyperus esculentus | 3 | 3 leaves. |
| 1) | Broad leafed | | |
| | Crops | | |
| | Cotton | 2 | 1 leaf |
| | Soya | 2 | 2 leaves. |
| 2) | Grass | | |
| | Crops | | |
| | Maize | 2 | 2–3 leaves |
| | Rice | 4 | 2–3 leaves |
| | Wheat | 5 | 2–3 leaves. |

The compounds used to treat the plants were applied to the plants as described in (a). A single pot of each crop and weed species was allocated to each treatment, with unsprayed controls and controls sprayed with acetone alone.

After treatment the pots were placed on capillary matting in a glass house, and watered overhead once after 24 hours and then by controlled sub-irrigation. Visual assessment of crop damage and weed control was made 20–24 days after spraying. The results were expressed as the percentage reduction in growth or damage to the crop or weeds, in comparison with the plants in the control pots.

The compounds of the invention, used at 1 kg/ha or less, have shown an excellent level of herbicidal activity together with crop tolerance on the weeds used in the foregoing experiments. When applied pre- or post-emergence at 1000 g/ha compounds 1 to 22 gave at least 90% reduction in growth of one or more of the weed species.

What is claimed:

1. A 4-benzoylisoxazole derivative of formula (I):

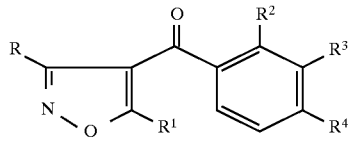

wherein:

R represents the hydrogen atom or a group —$CO_2R^5$;

$R^1$ represents a straight- or branched-chain alkyl group having up to three carbon atoms; cyclopropyl or 1-methylcyclopropyl;

$R^2$ represents:
a straight- or branched-chain alkyl group having up to four carbon atoms which is optionally substituted by one or more halogen atoms or one or more groups —$OR^{51}$;
a straight- or branched-chain alkoxy group having up to four carbon atoms which is optionally substituted by one or more halogen atoms; or
a group selected from —$S(O)_pR^{61}$, nitro and cyano;

$R^3$ represents a group —$S(O)_nR^6$;

$R^4$ represents:
a hydrogen, fluorine, chlorine or bromine atom;
a straight- or branched-chain alkyl group having up to four carbon atoms which is optionally substituted by one or more halogen atoms or one or more groups —$OR^{51}$;
a straight- or branched-chain alkoxy group having up to four carbon atoms which is optionally substituted by one or more halogen atoms, or
a group selected from —$S(O)_qR^{61}$, nitro, cyano and —$CO_2R^{52}$;

$R^5$ and $R^{61}$, which are the same or different, each represents a straight- or branched-chain alkyl group having up to six carbon atoms which is optionally substituted by one or more halogen atoms;

$R^{51}$ represents a straight- or branched-chain alkyl group having up to four carbon atoms which is optionally substituted by one or more halogen atoms;

$R^{52}$ represents a straight- or branched-chain alkyl group having up to four carbon atoms;

$R^6$ represents a straight- or branched-chain alkyl, alkenyl or alkynyl group having up to six carbon atoms which is optionally substituted by one or more halogen atoms;

n, p and q, are be the same or different, each represents zero, one or two;

provided that when $R^2$ represents —$S(O)_pR^{61}$ one of the groups n and p represents zero.

2. A compound according to claim 1 wherein $R^2$ represents:
a straight- or branched-chain alkyl group having up to four carbon atoms which is optionally substituted by one or more halogen atoms;
a straight- or branched-chain alkoxy group having up to four carbon atoms which is optionally substituted by one or more halogen atoms; or
a group —$S(O)_pR^{61}$;

$R^4$ represents:
a hydrogen, fluorine, chlorine or bromine atom;
a straight- or branched-chain alkyl group having up to four carbon atoms which is optionally substituted by one or more halogen atoms;
a straight- or branched-chain alkoxy group having up to four carbon atoms which is optionally substituted by one or more halogen atoms; or
a group —$S(O)_qR^{61}$;

$R^{61}$ represents a straight- or branched-chain alkyl group having up to four carbon atoms;

$R^5$ represents a straight- or branched-chain alkyl group having up to six carbon atoms;

$R^{52}$ represents a methyl or ethyl group;

$R^6$ represents a straight- or branched-chain alkyl, alkenyl or alkynyl group having up to four carbon atoms; and when $R^2$ represents —$S(O)_pR^{61}$, $R^4$ represents a group other than —$S(O)_qR^{61}$.

3. A compound according to claim 1 wherein:

$R^1$ represents a cyclopropyl group;

$R^2$ represents
an alkyl group containing one or two carbon atoms which is optionally substituted by one or more halogen atoms;
an alkoxy group having one or two carbon atoms which is optionally substituted by one or more halogen atoms; or
a group —$S(O)_pR^{61}$;

$R^4$ represents:
a fluorine, chlorine or bromine atom;
an alkyl group having one or two carbon atoms which is optionally substituted by one or more halogen atoms;
an alkoxy group having one or two carbon atoms which is substituted by one or more halogen atoms; or
a group —$S(O)_qR^{61}$;

$R^{61}$ represents a methyl or ethyl group;

$R^5$ represents a straight- or branched-chain alkyl group having up to six carbon atoms;

$R^{51}$ represents a methyl or ethyl group;

$R^{52}$ represents a methyl or ethyl group;

$R^6$ represents a methyl or ethyl group; and when $R^2$ represents —$S(O)_pR^{61}$, $R^4$ represents a group other than —$S(O)_qR^{61}$.

4. A compound according to claim 1 in which $R^1$ represents a cyclopropyl group.

5. A compound according to claim 1 wherein:

R represents hydrogen or —$CO_2Et$;

$R^1$ represents a cyclopropyl group;

$R^2$ represents
methyl, trifluoromethyl, methoxy or —$S(O)_pR^{61}$;

$R^3$ represents a group —$S(O)_nR^6$;

$R^4$ represents:
a chlorine or bromine atom; or
a group —$S(O)_qR^{61}$;

$R^6$ represents methyl, ethyl, propyl, chloromethyl or propenyl;

$R^{61}$ represents methyl;

and n, p and q independently represent zero, one or two.

6. A herbicidal composition which comprises as active ingredient a herbicidally effective amount of a compound of formula (I) as defined in claim 1 in association with an agriculturally acceptable carrier or diluent and/or surface active agent.

7. A herbicidal composition according to claim 6 which comprises 0.05 to 90% by weight of active ingredient.

8. A method for the control of growth of weeds at a locus which comprises applying to the locus a herbicidally effective amount of a compound of formula (I) as defined in claim 1.

9. A method according to claim 8 wherein the locus is an area used, or to be used, for growing crops and the compound is applied at an application rate from 0.01 kg to 4.0 kg per hectare.

10. A compound selected from the group consisting of:

4-[4-chloro-3-(methylsulphenyl)-2-trifluoromethylbenzoyl]-5-cyclopropylisoxazole;

4-[2,3-bis(methylsulphenyl)-4-bromobenzoyl]-5-cyclopropylisoxazole;

ethyl 4-[2,3-bis(methylsulphenyl)-4-chlorobenzoyl]-5-cyclopropylisoxazole-3-carboxylate;

4-[4-chloro-3-(ethylsulphenyl)-2-(methylsulphenyl)benzoyl]-5-cyclopropylisoxazole; and 4-[4-chloro-3-(chloromethylsulphenyl)-2-methoxybenzoyl]-5-cyclopropylisoxazole.

11. A 4-benzoylisoxazole derivative of formula (I):

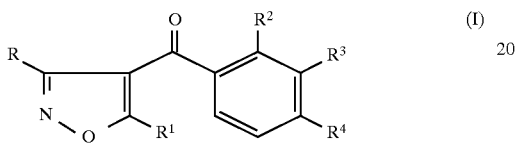

wherein:

R represents hydrogen or —$CO_2CH_2CH_3$;

$R^1$ represents cyclopropyl;

$R^2$ represents methyl; ethyl; propyl; isopropyl; methylsulphenyl; ethylsulphenyl; trifluoromethyl; methoxy; ethoxy; or isopropoxy;

$R^3$ represents methylsulphenyl; ethylsulphenyl; propylsulphenyl; isopropylsulphenyl; methylsulphenyl; ethylsulphenyl; methylsulphonyl; ethylsulphonyl; chloromethylsulphenyl; or chloromethylsulphenyl;

$R^4$ represents hydrogen; fluorine; chlorine; bromine; methylsulphonyl; or trifluoromethyl.

* * * * *